(12) United States Patent
Demos et al.

(10) Patent No.: US 8,945,440 B2
(45) Date of Patent: Feb. 3, 2015

(54) METHOD AND SYSTEM FOR PROCESSING OPTICAL MATERIALS FOR HIGH POWER LASER SYSTEMS

(75) Inventors: Stavros G. Demos, Livermore, CA (US); Rajesh Raman, Pleasanton, CA (US); Raluca A. Negres, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 622 days.

(21) Appl. No.: 13/240,980

(22) Filed: Sep. 22, 2011

(65) Prior Publication Data

US 2012/0073328 A1    Mar. 29, 2012

Related U.S. Application Data

(60) Provisional application No. 61/386,419, filed on Sep. 24, 2010.

(51) Int. Cl.
*B29D 11/00* (2006.01)
*G01N 21/59* (2006.01)

(52) U.S. Cl.
CPC .................................... *G01N 21/59* (2013.01)
USPC ....... 264/1.37; 264/1.32; 264/1.33; 264/1.34; 264/1.36; 264/1.7; 264/1.38; 264/1.6; 264/1.8; 264/1.9; 264/2.6; 264/2.7

(58) Field of Classification Search
USPC ............. 264/1.1, 1.27, 1.31, 1.32, 1.33, 1.34, 264/1.36, 1.37, 1.38, 1.6, 1.7, 1.8, 1.9, 2.6, 264/2.7
See application file for complete search history.

(56) References Cited

U.S. PATENT DOCUMENTS

| | | | |
|---|---|---|---|
| 5,507,799 | A | 4/1996 | Sumiya |
| 6,920,765 | B2 | 7/2005 | Menapace et al. |
| 2002/0046579 | A1 | 4/2002 | Peterson et al. |
| 2007/0156037 | A1 | 7/2007 | Pilon et al. |

FOREIGN PATENT DOCUMENTS

JP    2007-86047 A    12/2005

OTHER PUBLICATIONS

Raman, et al., "Time-resolved microscope system to image material response following localized laser energy deposition: exit surface damage in fused silica as a case example", Optical Engineering 50(1), 013602, 11 pages (Jan. 2011).
Raman, et al., "Kinetics of ejected particles during breakdown in fused silica by nanosecond laser pulses", Applied Physics Letters 98, 0151901, 4 pages (Jan. 31, 2011).
DeMange, et al., "Role of phase instabilities in the early response of bulk fused silica during laser-induced breakdown" Physical Review B 84, 054118, 7 pages (2011).

*Primary Examiner* — Jeffrey Wollschlager
*Assistant Examiner* — Stella Yi
(74) *Attorney, Agent, or Firm* — Kilpatrick Townsend & Stockton

(57) ABSTRACT

A method of determining conditioning pulse parameters for an optical element includes directing a pump pulse to impinge on the optical element and directing a probe pulse to impinge on the optical element. The method also includes determining a first time associated with an onset of electronic excitation leading to formation of an absorbing region of the optical element and determining a second time associated with expansion of the absorbing region of the optical element. The method further includes defining a turn-off time for a conditioning pulse between the first time and the second time. According to embodiments of the present invention, pulse shaping of the conditioning pulse enables laser conditioning of optical elements to achieve improvements in their laser induced damage threshold.

21 Claims, 8 Drawing Sheets

METHOD AND SYSTEM FOR PROCESSING OPTICAL MATERIALS FOR HIGH POWER LASER SYSTEMS

CROSS-REFERENCES TO RELATED APPLICATIONS

This application claims priority to U.S. Provisional Patent Application No. 61/386,419, filed Sep. 24, 2010, the disclosure of which is hereby incorporated by reference in its entirety for all purposes.

STATEMENT AS TO RIGHTS TO INVENTIONS MADE UNDER FEDERALLY SPONSORED RESEARCH OR DEVELOPMENT

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND OF THE INVENTION

Projections by the Energy Information Agency and current Intergovernmental Panel on Climate Change (IPCC) scenarios expect worldwide electric power demand to double from its current level of about 2 terawatts electrical power (TWe) to 4 TWe by 2030, and could reach 8-10 TWe by 2100. They also expect that for the next 30 to 50 years, the bulk of the demand of electricity production will be provided by fossil fuels, typically coal and natural gas. Coal supplies 41% of the world's electric energy today, and is expected to supply 45% by 2030. In addition, the most recent report from the IPCC has placed the likelihood that man-made sources of $CO_2$ emissions into the atmosphere are having a significant effect on the climate of planet earth at 90%. "Business as usual" baseline scenarios show that $CO_2$ emissions could be almost two and a half times the current level by 2050. More than ever before, new technologies and alternative sources of energy are essential to meet the increasing energy demand in both the developed and the developing worlds, while attempting to stabilize and reduce the concentration of $CO_2$ in the atmosphere and mitigate the concomitant climate change.

Nuclear energy, a non-carbon emitting energy source, has been a key component of the world's energy production since the 1950's, and currently accounts for about 16% of the world's electricity production, a fraction that could—in principle—be increased. Several factors, however, make its long-term sustainability difficult. These concerns include the risk of proliferation of nuclear materials and technologies resulting from the nuclear fuel cycle; the generation of long-lived radioactive nuclear waste requiring burial in deep geological repositories; the current reliance on the once through, open nuclear fuel cycle; and the availability of low cost, low carbon footprint uranium ore. In the United States alone, nuclear reactors have already generated more than 55,000 metric tons (MT) of spent nuclear fuel (SNF). In the near future, we will have enough spent nuclear fuel to fill the Yucca Mountain geological waste repository to its legislated limit of 70,000 MT.

Fusion is an attractive energy option for future power generation, with two main approaches to fusion power plants now being developed. In a first approach, Inertial Confinement Fusion (ICF) uses lasers, heavy ion beams, or pulsed power to rapidly compress capsules containing a mixture of deuterium (D) and tritium (T). As the capsule radius decreases and the DT gas density and temperature increase, DT fusion reactions are initiated in a small spot in the center of the compressed capsule. These DT fusion reactions generate both alpha particles and 14.1 MeV neutrons. A fusion burn front propagates from the spot, generating significant energy gain. A second approach, Magnetic fusion energy (MFE) uses powerful magnetic fields to confine a DT plasma and to generate the conditions required to sustain a burning plasma and generate energy gain.

Important technology for ICF is being developed primarily at the National Ignition Facility (NIF) at Lawrence Livermore National Laboratory (LLNL), assignee of this invention, in Livermore, Calif. There, a laser-based inertial confinement fusion project designed to achieve thermonuclear fusion ignition and burn utilizes laser energies of 1 to 1.3 MJ. Fusion yields of the order of 10 to 20 MJ are expected. Fusion yields in excess of 200 MJ are expected to be required in central hot spot fusion geometry if fusion technology, by itself, were to be used for cost effective power generation. Thus, significant technical challenges remain to achieve an economy powered by pure inertial confinement fusion energy.

Both refractive optical elements and reflective optical elements are widely used in laser systems to control the divergence of the laser beam (e.g., using lenses to focus the laser beam to a spot) or direct laser beams by changing the direction of propagation (e.g., using mirrors). Optical damage of optical components (i.e., laser induced damage) is a problem experienced during the operation of high power and/or intensity lasers. Damage can be manifested by failure of the material at laser fluences far below the intrinsic breakdown threshold of the materials, for example, at laser fluences one order of magnitude or more below the intrinsic breakdown threshold. Therefore, despite progress made in the reliability of high power laser systems, there is a need in the art for methods and systems to improve the laser induced damage thresholds of high power optical components and elements.

SUMMARY OF THE INVENTION

According to the present invention, techniques related to optical systems are provided. More particularly, an embodiment of the present invention provides methods and systems for processing optical elements. Merely by way of example, the invention has been applied to a method and system for conditioning optical elements to improve their laser induced damage threshold. The methods and systems described herein are also applicable to optical components utilized in numerous current and future high power optical systems including lasers, amplifiers, and the like.

According to an embodiment of the present invention, a method of determining conditioning pulse parameters for an optical element is provided. The method includes directing a pump pulse to impinge on the optical element, directing a probe pulse to impinge on the optical element, and determining a first time associated with an onset of electronic excitation leading to formation of an absorbing region of the optical element. The method also includes determining a second time associated with expansion of the absorbing region of the optical element and defining a turn-off time for a conditioning pulse between the first time and the second time.

According to another embodiment of the present invention, a method of laser conditioning an optical component is provided. The method includes a) positioning the optical component on a stage, b) determining a maximum conditioning fluence for the optical component, and c) determining a Nth fluence for an Nth conditioning phase. The method also includes d) providing a conditioning pulse having the Nth fluence, e) directing the conditioning pulse to impinge on a first portion of the optical component, f) directing the conditioning pulse to impinge on a subsequent portion of the optical component, and g) determining that the Nth fluence is less than the maximum conditioning fluence. The method further includes h) incrementing counter N and repeating c) through g) until the Nth fluence is equal to the maximum conditioning fluence.

According to a specific embodiment of the present invention, a system for conditioning an optical element is provided. The system includes a conditioning laser and a controller coupled to the conditioning laser. The controller is operable to provide, in conjunction with the conditioning laser, a conditioning pulse propagating along a beam path. The conditioning pulse is characterized by an ability to initiate an electronic excitation at defective regions to form confined absorbing regions but an inability to support an uncontrolled expansion of the confined absorbing region into host material to form laser induced damage sites. The system also includes optics disposed along the beam path and a stage operable to support the optical element along the beam path.

According to an embodiment of the present invention, a method to improve the damage threshold and damage resistance of the surface and bulk of optical components designed for high power laser applications is provided. The methods and techniques described herein are applicable to fused silica optical components as well as a variety of other optical materials, including KDP and DKDP nonlinear optical materials, various types of glass and crystalline optical materials, optical coatings for reflective or transmissive optical elements, ceramic optical materials, laser gain materials, and other material suitable for high intensity and/or power laser applications. The methods and techniques described herein are applicable in all cases in which laser-induced damage initiation results from the presence of defective sites associated with enhanced optical absorption or localized field intensification.

Embodiments of the present invention provide a method in which an optical element is pre-exposed to sub-damage threshold laser pulses that are characterized by predetermined tailored temporal profiles. In a specific embodiment, methods and systems are provided that choose a temporal profile for the pre-exposure pulse that provides benefits not available using conventional techniques.

Embodiments of the present invention can be utilized during the manufacturing of optical components for a variety of high power laser/amplifier systems. Specific examples include high power pulsed or CW laser systems and laser fusion systems including NIF and the Laser Inertial Fusion Energy (LIFE) system.

Pre-exposing KDP and DKDP crystals to laser pulses at slightly lower than operational fluence has been known to improve the damage behavior of the material. This process of pre-exposing the material to laser pulses to increase its damage threshold has been referred to as "laser conditioning." It has been recently shown that pulses on the order of 0.5 ns to 1 ns in duration offer the most efficient conditioning in KDP and DKDP materials. However, the mechanisms behind this process have not been fully understood. This type of laser conditioning has not been shown to be successful in improving the performance of any other material, either the bulk or the surface. In optical coatings, it has been shown that pre-exposure at lower fluences can lead to ejection of particles that were embedded in to the coating during the film deposition process. Furthermore, it is known that particles loosely attached on the surface of optical elements (such as dust) can be removed by exposure to a laser pulse, a process commonly referred to as "laser cleaning."

Embodiments of the present invention are distinct from the aforementioned processes in that embodiments of the present invention monitor and takes advantage of the interaction of the laser pulse with the defective region of the material to provide a method to deposit sufficient laser energy in to the defective area without allowing this to develop into a laser damage site. This is achieved by specially tailoring the temporal profile of the pre-exposure pulse to achieve control of the distinct processes of energy deposition leading to the modification of the defective region (damage precursor) to the subsequent phase of energy deposition into the host material leading to laser damage. This understanding has allowed the inventors to expand the use of laser conditioning to all optical materials using pre-exposure to conditioning pulses that have tailored temporal characteristics that can be experimentally measured and defined to be suitable for use in each difference material and application (e.g., bulk vs. surface).

Numerous benefits are achieved by way of the present invention over conventional techniques. For example, the present systems provide methods to condition optical elements to improve their laser induced damage thresholds, improving the reliability and performance of high power laser and amplifier systems utilizing these conditioned optics. Depending upon the embodiment, one or more of these benefits may be achieved. These and other benefits will be described in more detail throughout the present specification and more particularly below.

These and other objects and features of the present invention and the manner of obtaining them will become apparent to those skilled in the art, and the invention itself will be best understood by reference to the following detailed description read in conjunction with the accompanying drawings.

DETAILED DESCRIPTION OF THE INVENTION

It is generally accepted by the experts in the field that laser damage (i.e., laser-induced breakdown) can arise from the coupling of the laser (photon) power to defects located on or near the surface of the materials or even in the bulk of the materials. In high power laser systems, in which laser intensities can exceed $1\times10^{11}$ W/cm$^2$, absorption of energy by the defects can initiate a cascade process that can lead to exposure of the material to localized temperatures in the 1-100 eV range and initial pressures up to 10-1000 GPa, followed by the generation of a shock wave. The outcome of this exposure of the material to these extreme conditions is typically manifested as a microscopic crater on the surface or a microscopic void formed in the bulk of the material.

Embodiments of the present invention process optical components, such as optical components made using potassium dihydrogen phosphate (KDP) and deuterated KDP (DKDP) crystals, which are nonlinear optical materials suitable for beam control and frequency conversion in large aperture laser systems, to improve the damage performance (i.e., an increase in the damage threshold and a lower density of damage events for the same damage testing fluence) by using pre-exposure of the material to sub-damage threshold laser fluences. This process can be referred to as "laser conditioning." As described below, the inventors have determined that the laser conditioning efficiency is dependent, in part, on the temporal profile of the laser pulses used to perform laser conditioning.

Embodiments of the present invention can be used to effectively apply laser conditioning to a wide range of optical materials. The inventors have developed a step-by-step understanding of the laser damage timeline and are, therefore, able to identify the early processes that lead to laser conditioning prior to the activation of late processes that ultimately result in laser damage. As a result, embodiments of the present invention provide a pre-exposure pulse (i.e., a conditioning pulse) with a predetermined pulse shape having tailored temporal characteristics to activate the early processes and stop the evolution of subsequent late processes responsible for damage initiation. This selective activation of the processes involved during the damage timeline leads to strong modification of the defect structures responsible for laser induced damage with minimal influence on the host optical material. Without limiting embodiments of the present invention, the inventors believe that the prior modification of the defect structures responsible for laser induced damage reduce the ability of these defect structures to absorb the laser light from subsequent laser exposure, leading to materials with increased damage threshold and ability to operate at pre-determined operational laser parameters sustaining less or no laser induced damage.

To understand the damage timeline of exit surface damage in fused silica optical components, the inventors developed a multifunction microscope system capable of capturing high spatial and temporal resolution images of damage events through the entire damage timeline. Additional discussion related to the system developed by the inventors is provided in "Time-resolved microscope system to image material response following localized laser energy deposition: exit surface damage in fused silica as a case example," R. Raman et. al., Optical Engineering, 50, 013602 (2011), "Kinetics of ejected particles during laser-induced breakdown in fused silica," R. Raman et. al., Applied Physics Letters, 98, 051901, 2011, and "Role of phase instabilities in the early response of bulk fused silica during laser-induced breakdown," P. DeMange, et al., Phys. Rev. B, vol. 84, 054118-1-054118-7 (2011), the disclosure of which is hereby incorporated by reference in its entirety. Utilizing this system, the inventors have performed direct imaging of the localized dynamics of material response in bulk material following energy deposition via nanosecond-pulse laser-induced breakdown. Utilizing this system, the inventors have determined that localized, strongly absorbing regions, which start expanding during the laser pulse and result in crack generation and propagation, are established during the initial phases of the damage process. The surface of the optical component is observed to swell and erupt into a jet of microscopic particles of various sizes ranging from about 1 μm to about 50 μm with speeds ranging from about 3 km/s to about 10 m/s or less. The steps in the damage process clearly indicate that the host material is exposed to localized extreme conditions starting from the onset of the strong absorbing regions.

The inventors have determined that there is an early phase at which the defects responsible for damage initiation (also referred to as damage precursors) start absorbing energy, while the surrounding host material remains unaffected. However, as energy from the precursor region starts diffusing into the surrounding host material, the latter will become absorptive and result in the vast majority of the energy deposited in the material from the laser pulse creating the damage site. Utilizing the system discussed above, the time duration of the initial phase of the damage process before the host material becomes a strong absorber has been determined as a function of the physical and electronic properties of the precursor and host as well as the laser intensity, wavelength, and pulse shape.

Figure 1A:
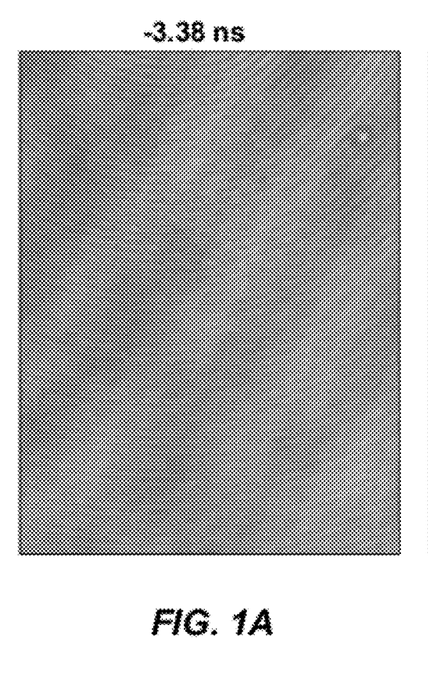
FIGS. 1A-1B are representative images of an optical element during a first stage of optical illumination according to an embodiment of the present invention.
Figure 1B:
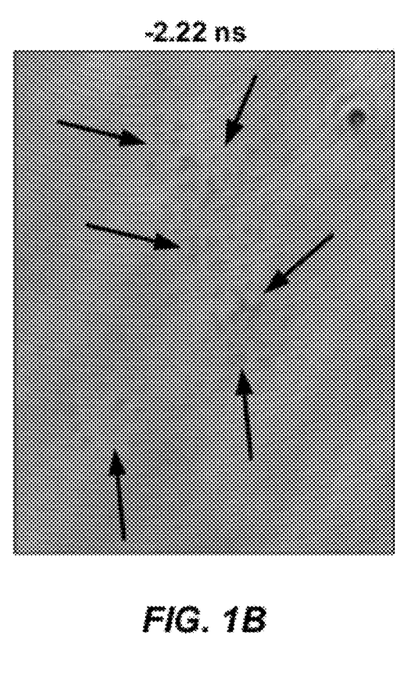

FIGS. 1A-1B are representative images captured on the surface of a commercially available fused silica flat during a first stage of optical illumination according to an embodiment of the present invention. As described more fully below, the images illustrated in FIGS. 1A-1B are associated with an early stage of a damage process. The images are captured for a single damage event at various times during the damage event using a pump/probe setup, although different damage sites could be used as well. The images shown in FIGS. 1A and 1B were obtained using strobe light illumination obtained by a probe laser having nearly Gaussian temporal shape with pulse duration of 150 ps at FWHM. Consequently, an image acquired at a negative time captures the transient state of the material before the peak of the pump pulse (i.e., the pulse causing damage to the material) is reached by the respective amount, i.e. denoted as negative delay.

Referring to FIG. 1A, an image captured at −3.38 ns with respect to the peak of the pump laser pulse is shown. At this early time, there is no observable change in the material. As the pump pulse intensity increases, a number of regions (i.e., "Gray" sites) appear for which the opacity of the material increases as shown at a time 2.22 ns before the peak of the laser pulse in FIG. 1B. The gray sites, which typically have a diameter ranging from about 1 μm to about 3 μm in diameter, are associated with reduced transmission (T) of the probe light passing through the optical element. Arrows in FIG. 1B are used to highlight the areas of reduced transmission that have developed by the time 2.22 ns before the peak of the pump laser pulse. As the pump laser pulse intensity continues to increase, the damage regions initially developing as gray sites grow to form damaged regions as shown in subsequent images.

Figure 1C:
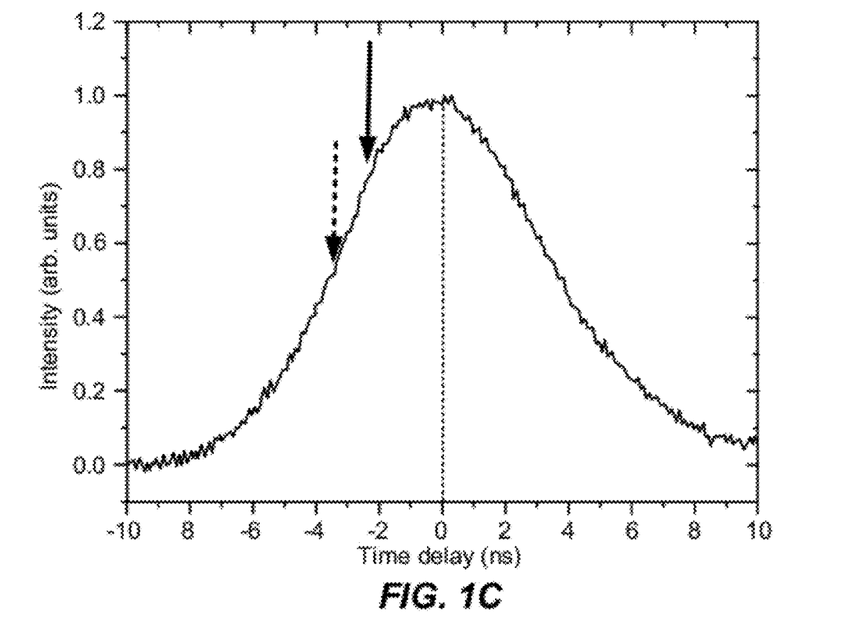
FIG. 1C is a simplified plot illustrating the intensity of an optical pulse as a function of time.

FIG. 1C is a simplified plot illustrating the intensity of an optical pulse generating the damage in the optical element as a function of time. Referring to FIG. 1C, the image in FIG. 1A is taken at the time indicated by the dashed arrow and the image in FIG. 1B is taken at the time indicated by the solid arrow. The laser pulse has a nearly Gaussian temporal shape with pulse duration of 7.8 ns at FWHM.

Figure 2A:
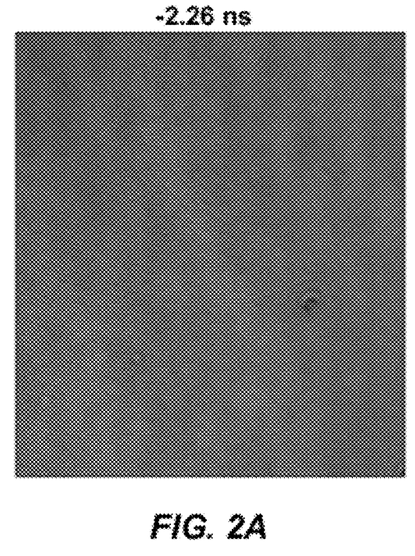
FIGS. 2A-2C are representative images of an optical element during a second and final stage of optical illumination according to an embodiment of the present invention.
Figure 2B:
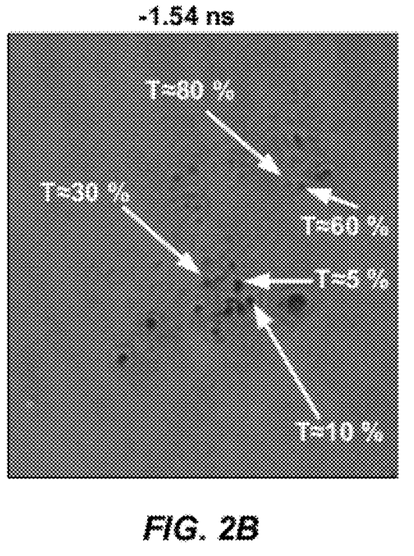
Figure 2C:
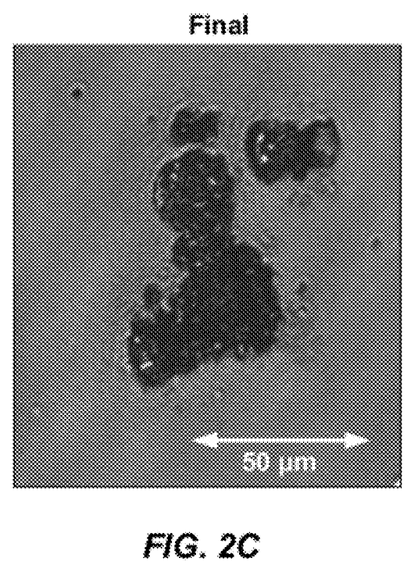

FIGS. 2A-2C are representative images of an optical element during a second and final stage of optical illumination according to an embodiment of the present invention. FIG. 2A is an image similar to FIG. 1B, but captured at 2.26 ns before the peak of the laser pulse. FIG. 2B is captured at a time of 1.54 ns before the peak of the laser pulse. As shown in FIGS. 2A and 2B, the increase in pulse intensity as time progresses result in the development and growth of the "gray" regions exhibiting increased transmission loss during image acquisition that may be assigned to increased absorption of the strobe probe pulse light. In FIG. 2A, the transmission loss varies as a function of position, indicating the formation of regions of material where an electronic excitation is present.

In FIG. 2B, a number of small sites exhibiting varying amounts of transmission loss (T denotes the percentage of transmitted probe light) ranging from 5% (site is highly absorbing) to 80% (low absorption) are present. In some images, the transmission is higher for low absorption regions, for example, 90%. Comparing FIG. 2A to FIG. 2B, the partial onset of the absorbing regions shown in FIG. 2A become more clearly visible in FIG. 2B indicating that, in fused silica surfaces and under the experimental excitation conditions used, the time duration between the onset of these absorbing regions and the time that these regions become strongly absorbing is on the order of 0.5 ns. FIG. 2C shows an image captured after the laser pulse that damages the material terminates (i.e., about 8 ns after the peak of the pulse). As shown by FIG. 2C, the inventor's experimental observations are confirmed, namely the first discernible changes in the material during a laser induced damage event are associated with the onset of an electronic excitation manifested as a reduction in transmission of light through the affected regions.

Figure 3A:
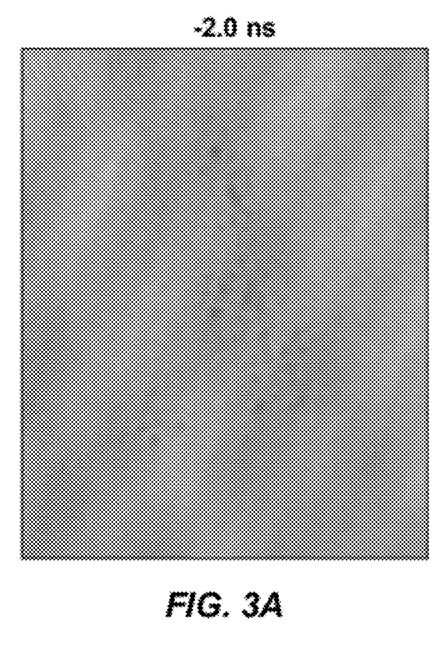
FIGS. 3A-3B are representative images of an optical element during the early phase of the damage initiation process, capturing the material modification stages that are allowed (FIG. 3A) and controlled (FIG. 3B) according to an embodiment of the present invention.
Figure 3B:
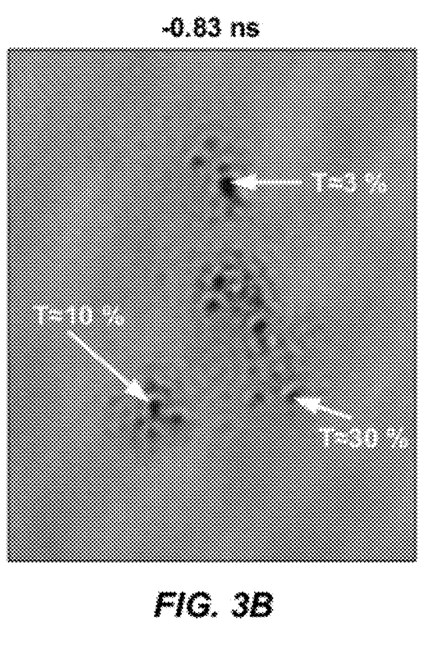
Figure 3C:
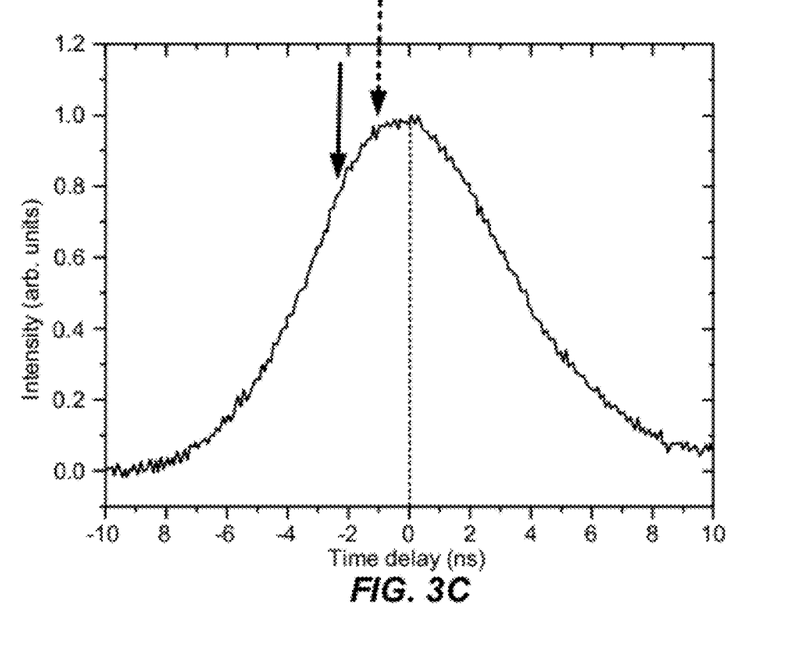
FIG. 3C is a simplified plot illustrating the intensity of an optical pulse as a function of time.

FIGS. 3A-3B are representative images of an optical element during a conditioning process according to an embodiment of the present invention. FIG. 3A shows an image similar to previous images, but captured at a slightly later delay. In FIG. 3A, the initial absorbing regions are observed in the image captured at 2.0 ns before the peak of the laser pulse. The same regions are observed in the image in FIG. 3B captured at 0.83 ns before the peak of the pulse. Comparison of these two transient images indicates that during the 1.17 ns separation in time between acquisition of these images, the absorbing regions exhibited an increase in their absorptivity (or reduction in the measured transmission T) while their physical size (diameter) was not significantly altered within experimental errors. This indicates that the absorptivity at regions of initial electronic excitation increases with time but no substantial increase in their size can be discerned. Referring to FIG. 3C, which plots the intensity of the laser pulse that produces damage in the optical element as a function of time, the time at which the image in FIG. 3A was captured (solid arrow) and the time at which the image in FIG. 3B was captured (dashed arrow) are illustrated.

It should be noted that if the pulse continues to be absorbed by the defects, the damage process continues. When the regions of electronic excitation (initiation sites) reach transmission losses of about 97%, the sites start to expand laterally (and axially). The rate at which the damage sites expand can be rapid, for example, expansion at a rate between 500 m/s and 5 km/s. The inventors have determined that the initiation sites will continue to grow in size, leading to the formation of the final damage sites shown in FIG. 2C. Additional results show that the ejection of material occurs as part of the damage process, leading to the formation of microscopic craters on the surface, commonly referred to as "surface damage sites."

Embodiments of the present invention benefit from the ability to quantify the extent of the host material modifications at various points in time. Specifically, before the initiation sites become absorbing and later start expanding, the small precursor material has only absorbed a very small amount of energy, therefore not causing any significant damage to the host material. This energy is locally deposited at the precursor site. This amount of energy is probably high enough to significantly alter the precursor by, for example, partially evaporating it and/or causing a spatial redistribution. Such changes will lead to a reduction in the ability of the precursor to initiate damage. In other words, from a practical point of view, this precursor will require a higher fluence to initiate damage than that prior to its modification. When the sites become strongly absorbing and start to expand, it is clear evidence for host material modifications that subsequently drive the energy deposition process. Therefore, in order to achieve the altered state of such precursors, embodiments of the present invention promptly stop the energy deposition before the host material becomes absorptive. This is achieved by "switching off" the laser power at the appropriate time to avoid further energy deposition into the absorbing sites and therefore halt the damage process before the host material becomes absorptive and the regions of initial electronic excitation begin to grow in size.

Referring to FIG. 3C, it would be desirable to switch off, also referred to as clipping, the conditioning laser power at a time period preceding the initial expansion of the absorbing regions. According to embodiments of the present invention, the pre-exposure (conditioning) pulses are temporally shaped such that the energy deposition at the precursors fully develops, while minimal energy deposition and modification is allowed to take place in the surrounding host material.

Figure 4:
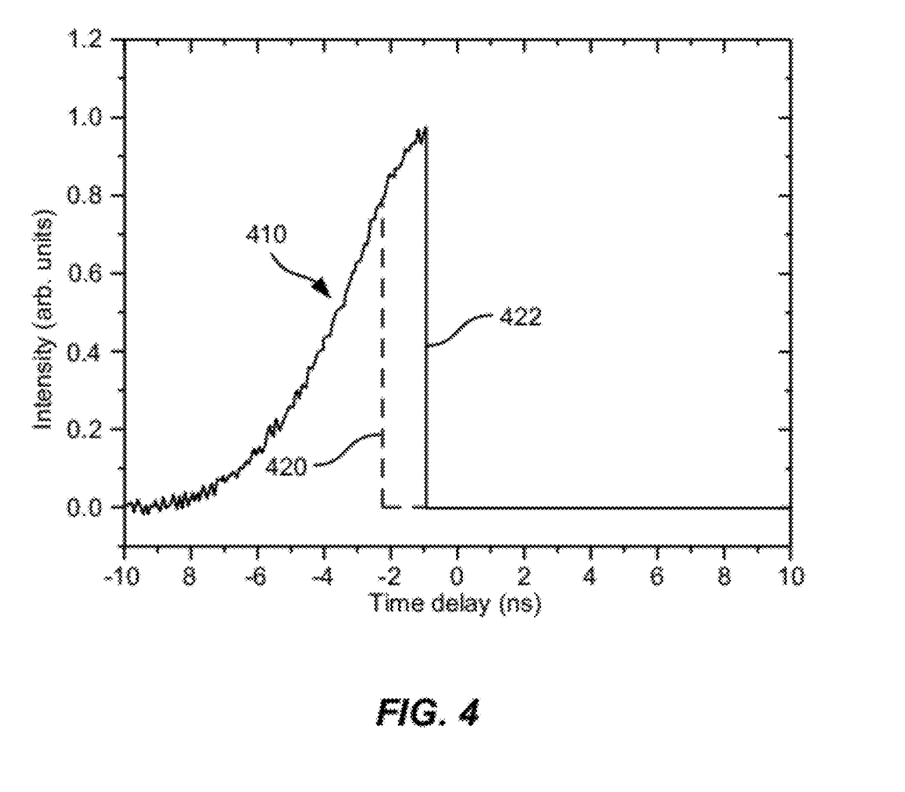
FIG. 4 is a simplified plot illustrating pulse shapes useful for laser conditioning of optical components according to an embodiment of the present invention.

FIG. 4 is a simplified plot illustrating a pulse shape useful for conditioning of optical elements according to an embodiment of the present invention. As illustrated in FIG. 4, the pre-exposure conditioning laser pulse, which can be a modified version of the pulse to which the optical element is eventually exposed (operational pulse), has a rising leading edge. In the illustrated embodiment, the rising leading edge is a portion of a substantially Gaussian pulse or a portion of the operational pulse. When the pulse intensity reaches a predetermined value at a predetermined time prior to the peak of the pulse, the intensity is rapidly reduced, for example, to zero, as shown in FIG. 4. Two alternative pulse profiles are illustrated in FIG. 4, a dashed trailing edge corresponding to the time illustrated in FIG. 3A and a solid trailing edge corresponding to the time illustrated in FIG. 3B. As will be evident to one of skill in the art, the trailing edge may have a finite decay time as appropriate to the method used to reduce the laser intensity without allowing the development of laser induced damage. As an example, if a shutter is used to block the laser light, the time constant associated with the shutter will be observed in the decay time of the laser pulse. The shutter can alternatively be referred to as a trailing edge pulse shaping unit. One of ordinary skill in the art would recognize many variations, modifications, and alternatives.

According to an embodiment of the present invention, the laser power is increased gradually, for example, using the leading edge of a temporally Gaussian pulse, and then rapidly switched off upon reaching a predetermined excitation level (e.g., intensity). In some embodiments, the turn-off (decay) time is small (e.g., on the order of a few picoseconds or less). In other embodiments, the turn-off time can be increased as appropriate to the particular materials utilized for the optical components. This parameter is useful in achieving optimal "conditioning" results using this method. The turn-off time can be linear or nonlinear as appropriate to the particular conditioning process.

The pre-exposure conditioning pulse can be characterized by a number of parameters which include a) the leading edge pulse shape, b) the leading edge pulse duration, c) the peak intensity, d) the time of peak intensity and, e) the turn-off (decay) time of the pulse. The temporal profile of the leading edge might be similar to that of the pulse at operational conditions for reason discussed below. The temporal duration of this leading edge might vary but assuming a near Gaussian pulse shape, it might be allowed to develop at about 80% of peak intensity as shown by the arrows in FIG. 1C and FIG. 3C. The peak intensity will be a function of the operational intensity or laser fluence and can be a single value or a range of values as will be discussed in more detail below. The turn-off (decay) time of the pulse takes place fast enough so that the sites initially exhibiting absorption (visible via imaging as "gray" areas) do not develop into an expanding volume of modified material. In some embodiments, the conditioning pulse decay time is very short, although practically this may be difficult to achieve. Just the fact that the intensity of the pulse is reduced is not sufficient to avoid damage initiation. This is because although the intensity is reduced, the absorptivity of the localized regions might have increased by orders of magnitude and the energy deposited might remain very high. One way to determine the minimum decay time for a specific material is by performing appropriate measurement (such as those depicted in FIGS. 1A-3C) to monitor the behavior of the "gray" low absorbing modified regions during the decay of the laser pulse. If the energy deposition is not arrested fast enough, the process will lead to damage sites on the optic although probably not as large as those if the pulse was not turned off at all. In summary, assuming that the leading part of the conditioning pulse will have a pulse shape similar to that of the operational pulse, embodiments of the present invention define a) the leading edge time duration of the pulse, b) the decay time and, c) the conditioning pulse peak intensity (or range of intensities). These parameters can be referred to as the "Conditioning Pulse Parameters" or CPPs. The turn-off time and the decay time of the pulse can be defined in relation to the time at which the decrease of the pulse intensity starts and the time interval from the start of the pulse intensity decrease to the time that the intensity becomes zero (or 1/e of the peak or another suitable power level), respectively.

Given that optical materials are designed to operate in various wavelength ranges and pulse durations, there are different precursor populations leading to damage initiation under diverse excitation conditions. Therefore, in some implementations, similar excitation conditions are utilized for both conditioning and normal laser operation (e.g., wavelength, pulse durations, pulse shapes, and the like) in order to access the relevant precursor populations. The inventors have determined that the use of shorter wavelengths (i.e., higher photon energy) and shorter pulses (i.e., higher laser intensities) can provide some benefits depending on some particular materials. When the conditioning pulse reaches an intensity at which local deposition of energy occurs at the defective site, but prior to expansion into the bulk material, the conditioning pulse is switched off. The optic can then be scanned with these customized temporally shaped pulses. The scan should cover the entire surface area or volume of the material. It would be then beneficial to rescan the material possibly multiple times using increasing fluences for each rescan operation. This will lead to the destruction or partial passivation of all precursors that would lead to damage initiation over a wide range of fluences, leading to a material with improved damage resistance. Utilizing embodiments of the present invention, the conditioning process produces small to negligible changes in the optical quality of the optical element (e.g., surface roughness, scattering of light, or the like) while improving the damage resistance of the optical element. In some embodiments, the changes produced by embodiments of the present invention may be visible using as high resolution microscope system (such as a scanning electron microscope).

Figure 5:
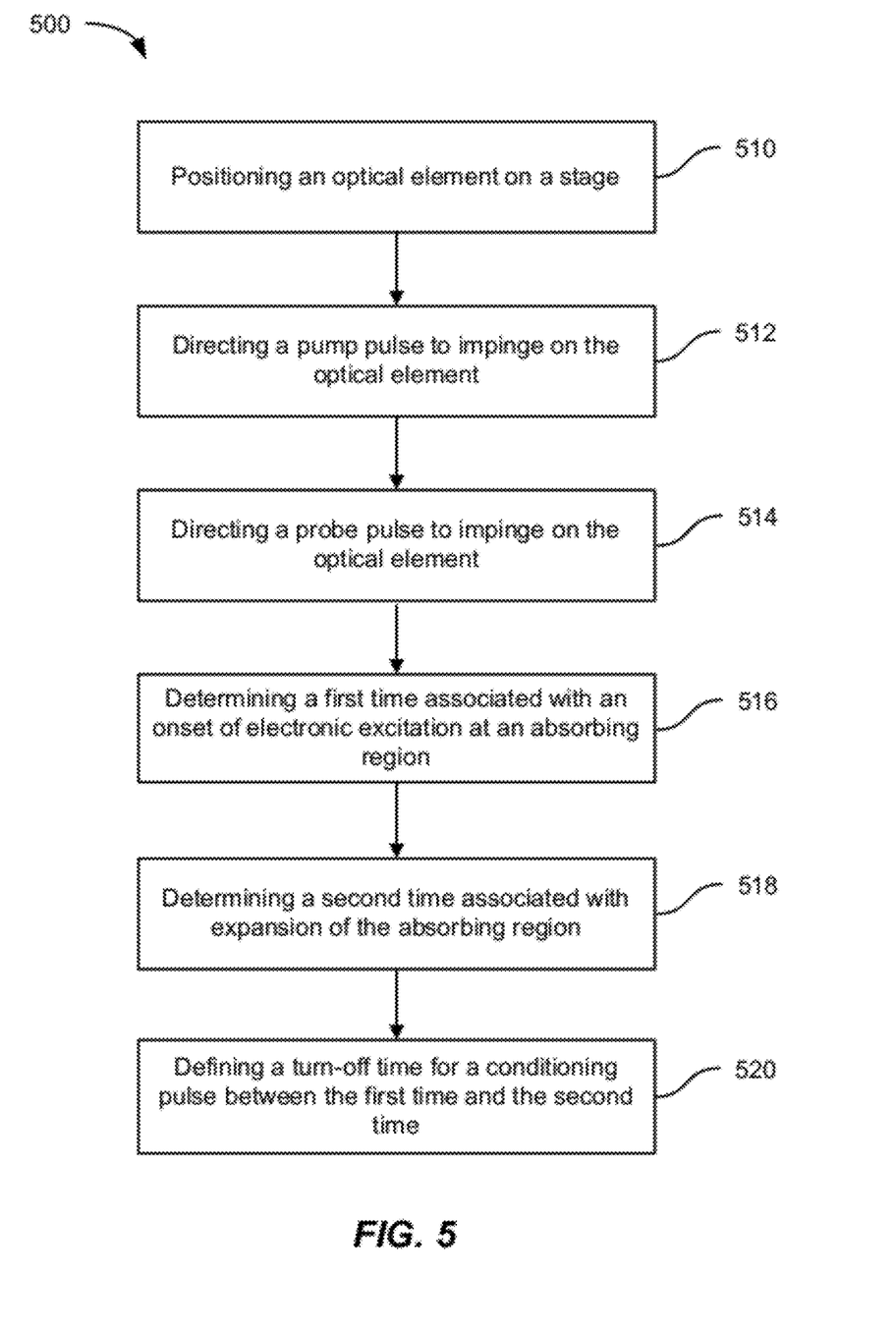
FIG. 5 is a simplified flowchart illustrating a method of determining conditioning pulse characteristic parameters for an optical element according to an embodiment of the present invention.

FIG. 5 is a simplified flowchart illustrating a method of determining conditioning pulse parameters for an optical element according to an embodiment of the present invention. The method 500 includes positioning the optical element on a stage (510). In an embodiment, the optical element is one of a variety of optical components such as a lens, a mirror, a gain medium such as an amplifier slab, a non-linear optical element such as a frequency doubling crystal, a KDP optical component, a DKDP optical component, or the like. In some embodiments, the stage is moveable to position the optical element with respect to the laser beam. In other embodiments, the laser beam is scanned over a fixed optical element or a combination of motion of the beam and/or the optical element is utilized.

The method also includes directing a pump pulse to impinge on the optical element (512) and directing a probe pulse to impinge on the same location of the optical element (514). In an embodiment, the pump pulse is modified to form a conditioning pulse used to condition the optical element. The pump pulse can be characterized by various pulse parameters including the pulse shape, peak intensity, and the like. In some embodiments, the pump pulse has sufficient intensity and fluence to produced optical damage in the optical element. Typically, the pulse width of the probe pulse is a fraction of the pulse width of the pump pulse and short enough to resolve the onset of the electronic excitation and subsequent expansion of the absorbing region. As described above, the probe pulse is scanned in time with respect to the pump pulse to obtain time resolved images of the optical element as the intensity of the pump pulse increases towards the peak intensity of the pump pulse.

Using the pump and probe pulses, a first time associated with an onset of electronic excitation at an absorbing region is determined (516). As illustrated in FIG. 3C, the time can be associated with an intensity and fluence related to the shape of the leading edge of the pump pulse. With progression in time, regions of the optical element will begin to absorb light as a result of electronic excitation. The drop in transmission can be measured as the absorptivity at the regions of electronic excitation initially increases with time while the size of the absorbing region is substantially unchanged. Determining the first time associated with the onset of electronic excitation can include imaging at least the absorbing region and determining a predetermined decrease in transmission through the absorbing region, for example a decrease in transmission exceeding 5%, although other percentages can be utilized as appropriate to the particular application.

A second time associated with expansion of the absorbing region is also determined (518). As illustrated in FIG. 3B, the lateral extent of the absorbing regions begins to increase, indicating that significant amount of energy from the laser pulse is transferred to the bulk material surrounding the initial region of electronic excitation. The expansion of the absorbing regions is thus related to damage of the optical element. Determining the second time associated with expansion of the absorbing region can include imaging at least the absorbing region and determining a predetermined increase in spatial extent of the absorbing region. Determining the second time associated with expansion of the absorbing region can alternatively include imaging at least the absorbing region and determining a predetermined decrease in transmission through the absorbing region of greater than 80%.

A turn-off time for a conditioning pulse is defined at a time between the first time and the second time (520). In some embodiments, the peak intensity of the conditioning pulse is defined as the intensity of the pump pulse at operational conditions at the first time determined in step 516.

In an embodiment, a pulse similar in shape to the pulse illustrated in FIG. 4 is utilized, with the decrease in intensity associated with the trailing edge (turn-off) taking place gradually. Starting with a very short decay time (on the order of a few ps), the decay time can be increased while the leading edge of the conditioning pulse is set so that the initial electronic excitation (observation of "gray" areas is taking place. The progression of these grays areas is subsequently monitored as a function of the decay time. The maximum allowable decay time is defined as that when the conditioning pulse turn-off is not fast enough to avoid expansion of the absorbing regions and formation of laser induced damage sites.

In another embodiment, a pulse similar in shape to the pulse illustrated in FIG. 4 is utilized, with the decrease in intensity associated with the trailing edge (turn-off) initially positioned shortly after the leading edge of the pulse begins, for example the trailing edge 422 is positioned slightly after −8 ns. The trailing edge 422 is subsequently moved forward in time, enabling the peak intensity to grow. In this case, the conditioning pulse does not initiate the electronic excitation in the defective areas of the optical element because the peak fluence is too low. The trailing edge is then moved forward in time, and as the trailing edge approaches line 420, absorption is observed due to electronic excitation. Preconditioning of the optical element can then be performed at peak intensities between that obtained using line 420 and that obtained using line 422.

In some embodiments, the onset of electronic excitation is associated with a first intensity of the pump pulse and the expansion of the absorbing region is associated with a second intensity of the pump pulse. In a particular embodiment, the method also includes determining a fluence of the pump pulse associated with damage of the optical element, which may be performed prior to directing the pump and probe pulses to impinge on the optical element. As illustrated in FIG. 4, the pump pulse may be characterized by a Gaussian leading edge and a non-Gaussian trailing edge.

It should be appreciated that the specific steps illustrated in FIG. 5 provide a particular method of determining conditioning pulse parameters for an optical element according to an embodiment of the present invention. Other sequences of steps may also be performed according to alternative embodiments. For example, alternative embodiments of the present invention may perform the steps outlined above in a different order. Moreover, the individual steps illustrated in FIG. 5 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 6:
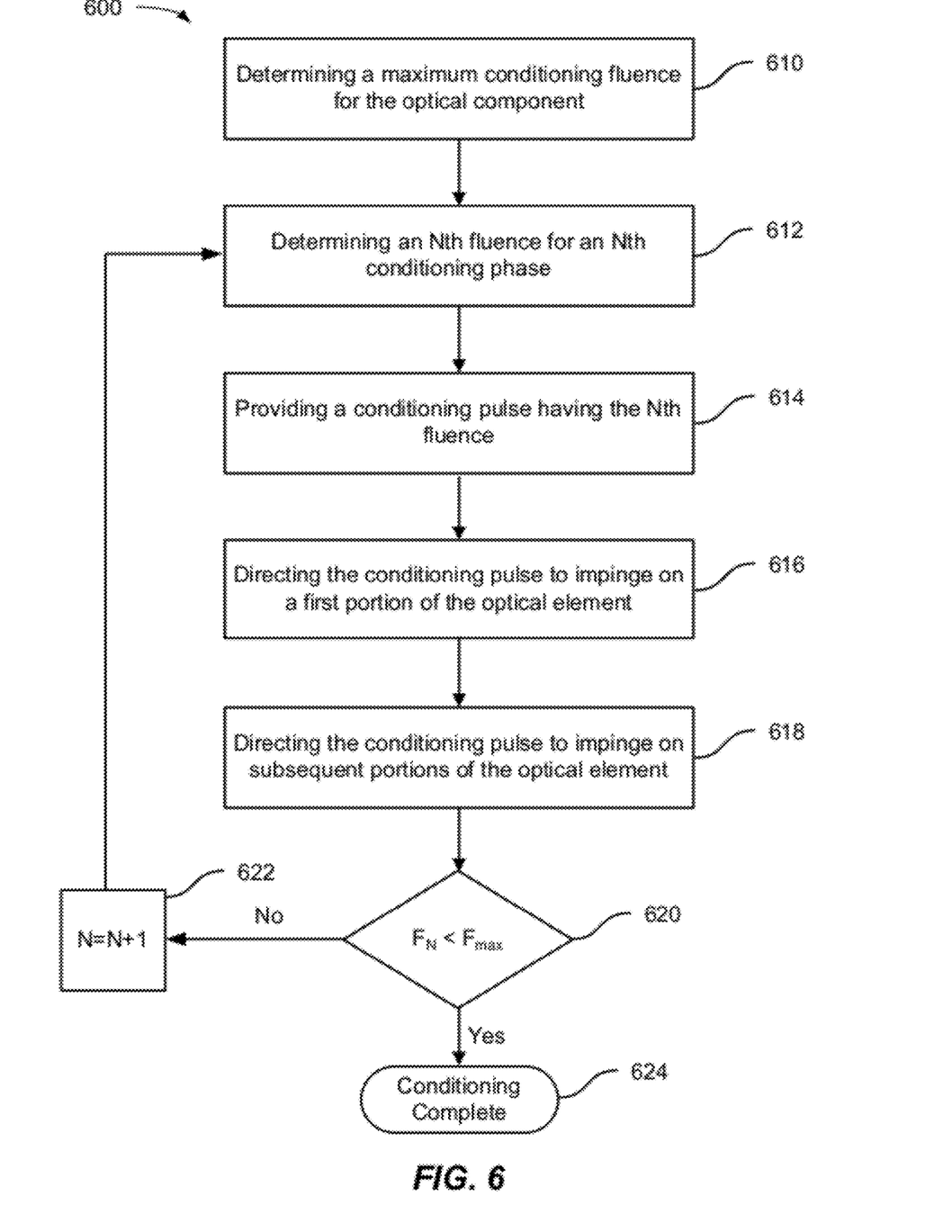
FIG. 6 is a simplified flowchart illustrating a method of laser conditioning an optical component according to another embodiment of the present invention.

FIG. 6 is a simplified flowchart illustrating a method of conditioning an optical element according to another embodiment of the present invention. The method 600 includes positioning an optical element on a stage (e.g., a moveable stage) and determining a maximum conditioning fluence for the optical element (610), which can be a gain element or a non-linear optical element. In addition, other conditioning pulse parameters are defined as described more fully below. Determining the maximum conditioning fluence can include determining a temporal profile of the conditioning pulse since the fluence is a function of the temporal pulse shape and the intensity (i.e., the integral of the intensity over time). The method also includes determining an Nth fluence for an Nth conditioning phase (612). In an embodiment, results of a previous analysis that was performed using the optical element are retrieved from a memory to determine the fluence appropriate for a use with a first conditioning phase (N=1). In another embodiment, the peak intensity of the conditioning pulse is increased corresponding to small values of the pump pulse towards values that would result in damage to the optical element. As the peak intensity is increased, measurements of the optical element can be performed to ensure that the conditioning process passivates the precursors over a range of conditioning pulse peak intensities that cover the operational fluences of the system designed. Alternatively, the peak intensity of the conditioning pulse may be continuously increased to as high as possible to explore the limits of the technique and improve the damage threshold of the material to its maximum possible level.

A conditioning pulse having the Nth fluence is provided (614) and the conditioning pulse is directed to impinge on a first portion of the optical element (616). Providing the conditioning pulse can include providing a pulse having a Gaussian temporal profile characterized by a peak intensity at a peak time and clipping the pulse at a time prior to the peak time. An onset of absorption in the optical component can be determined and the pulse can be clipped at a time less than 1 ns after the onset of absorption.

The conditioning pulse is then directed to impinge on subsequent portions of the optical element (618). In an embodiment, the optical element is scanned on a moveable stage. In other embodiments, the conditioning pulse is scanned, for example, raster scanned, across the optical element. In some embodiments, determining the fluence used during conditioning comprises scanning of a beam across the optical element, since the threshold for electronic excitation without expansion into the bulk may vary as a function of position on the optical element. As the conditioning pulse impinges on subsequent portions of the optical element, the damage resistance of the optical element is increased as the precursors that could have initiated damage during operation are passivated and/or removed.

If the Nth fluence associated with the Nth conditioning phase is less than the maximum fluence for the optical components (e.g., the fluence associated with the laser pulse during operation), then a determination can be made that the scanning of the optical element is not complete (620) and a subsequent phase of the conditioning process can be performed by incrementing the counter (N=N+1) (622)) and repeating the conditioning process at the next fluence level. When the fluence for conditioning has reached the maximum conditioning fluence for the optical component, then the conditioning process is completed (624).

It should be appreciated that the specific steps illustrated in FIG. 6 provide a particular method of conditioning an optical element according to an embodiment of the present invention. Other sequences of steps may also be performed according to alternative embodiments. For example, alternative embodiments of the present invention may perform the steps outlined above in a different order. Moreover, the individual steps illustrated in FIG. 6 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 7:
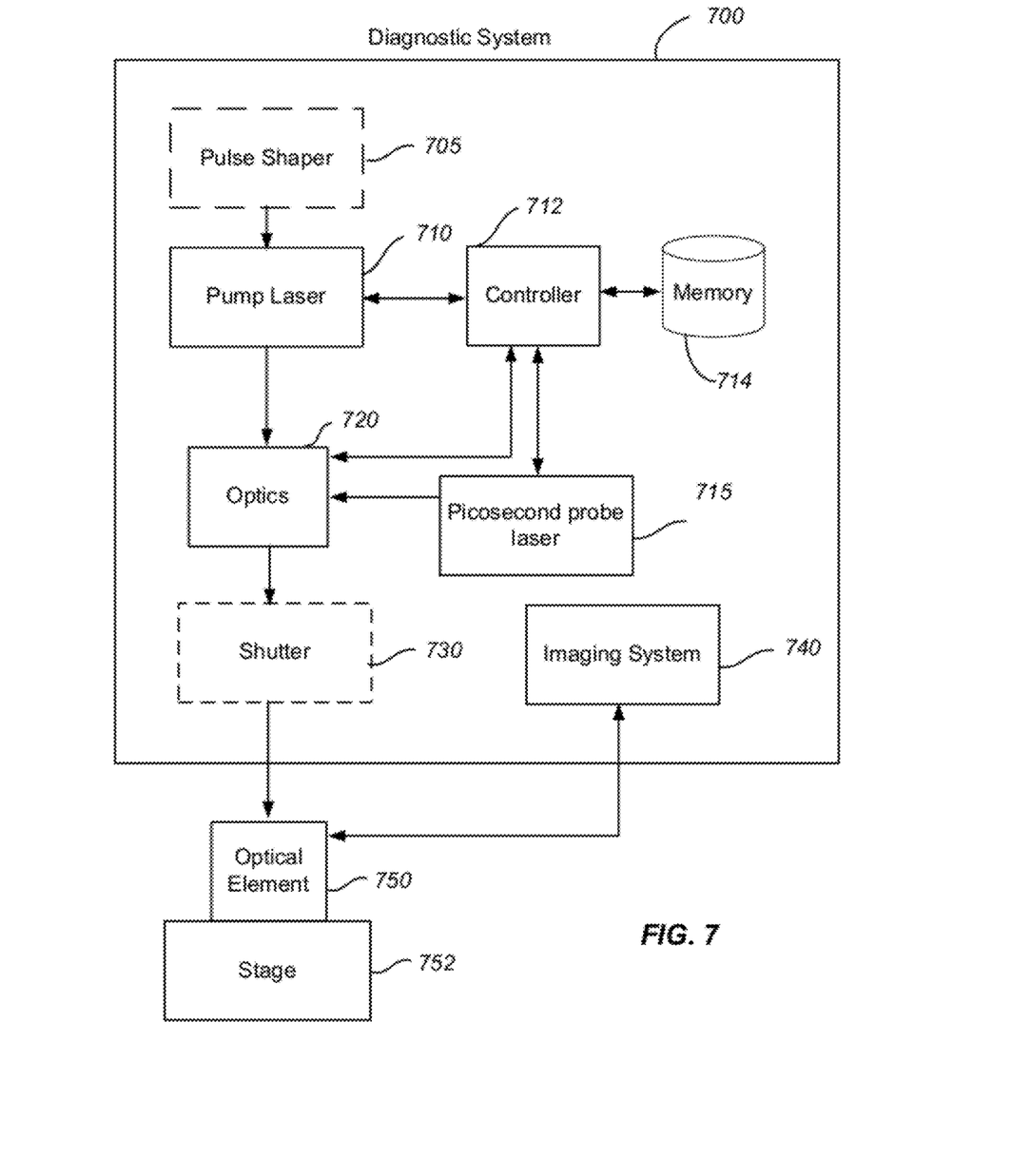
FIG. 7 is a simplified schematic diagram of a diagnostic system according to an embodiment of the present invention.

FIG. 7 is a simplified schematic diagram of a diagnostic system according to an embodiment of the present invention. The diagnostic system 700 includes a pump laser 710, which may be a laser with which the optical element is utilized during operation. In this case, the optional pulse shaper 710, optics 720 or the optional shutter 730 are utilized to provide a variable pulse peak intensity and intensity temporal profile with a peak intensity less than or equal to the peak intensity of the laser during operation. As discussed above, the shutter could be aligned with the leading edge of the pulse from laser 710 and then shifted forward in time, using, for example, an optical delay stage, to provide conditioning pulses of gradually increasing peak intensity and fluence. In other embodiments, the conditioning laser is a laser with variable intensity output that can be initially operated at a low peak intensity and then operated to provide a gradually increasing peak intensity. One of ordinary skill in the art would recognize many variations, modifications, and alternatives.

The diagnostic system 700 also includes a controller 712 coupled to the conditioning laser 710 and a picosecond probe laser 715. The controller 712 can include a processor that is used to perform calculations related to positioning of the optical element 750 using the stage 752, the peak intensity or fluence of the conditioning laser, optical delay between the pulses from the conditioning laser and the probe laser, beam steering using optics 720, shuttering of portions of the pulses using optional shutter 730, raster scanning of the conditioning laser beam with respect to the optical element, and other system parameters. A memory 714 (also referred to as a computer readable medium or a database) is coupled to the controller 712 in order store data used by the processor and other system elements. The controller 712 can interact with an imaging system 740, which provides data on the absorption characteristics of the optical element, providing images as illustrated in FIG. 2A and the like.

The controller 712 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the present invention in software, firmware and/or hardware. As an example, such processors include dedicated circuitry, ASICs, combinatorial logic, other programmable processors, combinations thereof, and the like.

The memory 714 can be local or distributed as appropriate to the particular application. Memory 714 may include a number of memories including a main random access memory (RAM) for storage of instructions and data during program execution and a read only memory (ROM) in which fixed instructions are stored. Thus, memory 714 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

Figure 8:
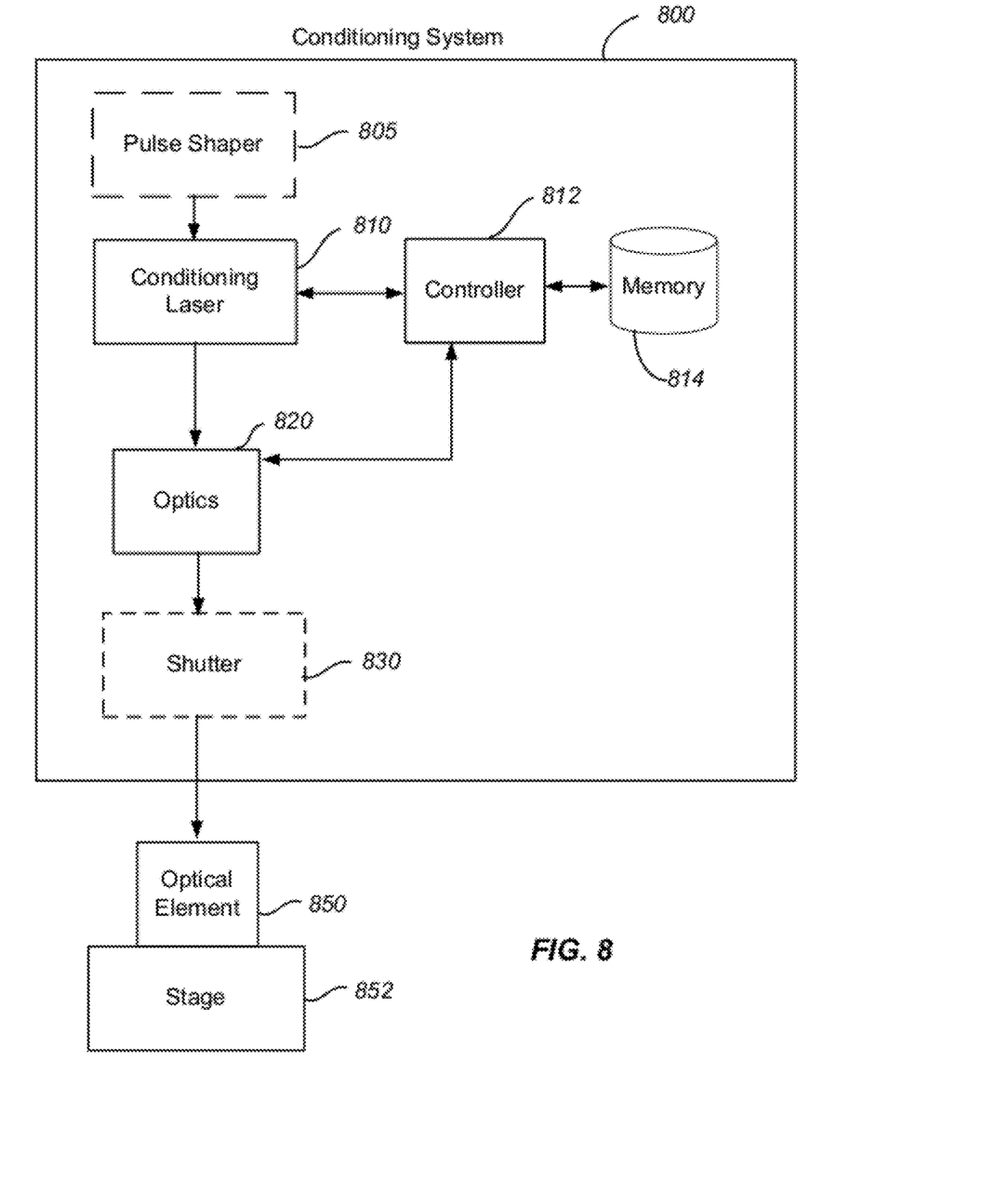
FIG. 8 is a simplified schematic diagram of a conditioning system according to an embodiment of the present invention.

FIG. 8 is a simplified schematic diagram of a conditioning system according to an embodiment of the present invention. The conditioning system in FIG. 8 shares some common elements with the diagnostic system 700 illustrated in FIG. 7 and description related to these common element is not repeated for purposes of brevity. The conditioning system 800 includes an optional pulse shaper 805 and a conditioning laser 810, which may be a laser with which the optical element is utilized during operation. Optics 820 and/or the optional shutter 830 are utilized to provide a variable fluence pulse with a fluence less than or equal to the maximum fluence appropriate for the optical element being conditioned. As discussed in relation to FIG. 7, the shutter could be aligned with the leading edge of the pulse from conditioning laser 810 and then shifted forward in time, using, for example, an optical delay stage, to provide conditioning pulses of gradually increasing peak intensity and fluence. In other embodiments, the conditioning laser is a laser with variable intensity output that can be initially operated at a low peak intensity and then operated to provide a gradually increasing peak intensity. One of ordinary skill in the art would recognize many variations, modifications, and alternatives. The conditioning system 800 also includes a controller 812 coupled to the conditioning laser 810 and a memory 814. Using the conditioning system illustrated in FIG. 8, the damage resistance of the optical element can be increased using the methods described herein.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of determining conditioning pulse parameters for an optical element, the method comprising:
    directing a pump pulse to impinge on the optical element;
    directing a probe pulse to impinge on the optical element;
    determining a first time associated with an onset of electronic excitation leading to formation of an absorbing region of the optical element;
    determining a second time associated with expansion of the absorbing region of the optical element; and
    defining a turn-off time for a conditioning pulse between the first time and the second time.

2. The method of claim 1 wherein the onset of electronic excitation is associated with a first fluence of the pump pulse.

3. The method of claim 1 wherein the expansion of the absorbing region is associated with a second fluence of the pump pulse.

4. The method of claim 1 further comprising determining a fluence of the pump pulse associated with damage of the optical element.

5. The method of claim 1 wherein the pump pulse is characterized by a Gaussian leading edge.

6. The method of claim 5 wherein the pump pulse comprises a non-Gaussian trailing edge.

7. The method of claim 1 wherein determining the first time associated with the onset of electronic excitation comprises:
    imaging at least the resulting absorbing region; and
    determining a predetermined decrease in transmission through the absorbing region.

8. The method of claim 7 wherein the predetermined decrease in transmission exceeds 5%.

9. The method of claim 1 wherein determining the second time associated with expansion of the absorbing region comprises:
    imaging at least the absorbing region; and
    determining a predetermined increase in spatial extent of the absorbing region.

10. The method of claim 1 wherein determining the second time associated with expansion of the absorbing region comprises:
   imaging at least the absorbing region; and
   determining a predetermined decrease in transmission through the absorbing region of greater than 80%.

11. The method of claim 1 wherein the optical element comprises at least one of a gain element, a non-linear optical element, a transmissive element, a reflective element, or a portion of an element.

12. The method of claim 1 wherein expansion of the absorbing region of the optical element occurs at a rate between 500 m/s and 5 km/s.

13. The method of claim 1 further comprising defining a decay time for the conditioning pulse.

14. A method of laser conditioning an optical component, the method comprising:
   a) positioning the optical component on a stage;
   b) determining a maximum conditioning fluence for the optical component;
   c) determining a Nth fluence for an Nth conditioning phase;
   d) providing a conditioning pulse having the Nth fluence;
   e) directing the conditioning pulse to impinge on a first portion of the optical component;
   f) directing the conditioning pulse to impinge on a subsequent portion of the optical component;
   g) determining if the Nth fluence is less than the maximum conditioning fluence; and
   h) incrementing counter N and repeating c) through g) until the Nth fluence is equal to the maximum conditioning fluence.

15. The method of claim 14 wherein the stage comprises a moveable stage.

16. The method of claim 14 wherein determining the maximum conditioning fluence comprises determining a temporal profile of the conditioning pulse.

17. The method of claim 14 wherein providing the conditioning pulse comprises:
   providing a pulse having a rising temporal profile similar to that at operational conditions characterized by a peak intensity at a peak time; and
   clipping the pulse at a time prior to the peak time.

18. The method of claim 14 wherein providing the conditioning pulse comprises:
   providing a pulse having at least one of a Gaussian or Lorenzian temporal profile characterized by a peak intensity at a peak time; and
   clipping the pulse at a time prior to the peak time.

19. The method of claim 18 further comprising determining an onset of absorption in the optical component, wherein clipping the pulse is performed at a time less than 1 ns after the onset of absorption.

20. The method of claim 14 wherein directing the conditioning pulse to impinge on a subsequent portion of the optical component comprises raster scanning the conditioning pulse across the optical component.

21. The method of claim 14 wherein the optical element comprises at least one of a gain element, a non-linear optical element, a transmissive element, a reflective element, or a part of an element.

* * * * *